United States Patent [19]

Kaule et al.

[11] 4,144,767

[45] Mar. 20, 1979

[54] METHOD AND APPARATUS FOR PRODUCING PULSE-SHAPED ACOUSTIC WAVES ON A WORKPIECE SURFACE

[75] Inventors: Walter Kaule; Erik Primbsch, both of Cologne, Fed. Rep. of Germany

[73] Assignee: Krautkramer-Branson, Inc., Stratford, Conn.

[21] Appl. No.: 856,338

[22] Filed: Dec. 1, 1977

[30] Foreign Application Priority Data

Feb. 24, 1977 [DE] Fed. Rep. of Germany ....... 2707933

[51] Int. Cl.² ............................................. G10N 29/04
[52] U.S. Cl. ...................................................... 73/643
[58] Field of Search ................. 73/612, 625, 626, 628, 73/641, 643

[56] References Cited

U.S. PATENT DOCUMENTS

| | | | |
|---|---|---|---|
| 3,166,731 | 1/1965 | Joy | 73/626 |
| 3,251,220 | 5/1966 | Joy | 73/625 |
| 3,978,713 | 9/1976 | Penney | 73/643 X |
| 4,080,838 | 3/1978 | Kuroda et al. | 73/612 |

OTHER PUBLICATIONS

J. Krautkramer et al., Werkstoffprufung mit Ultraschall, 3rd Ed., Springer-Verlag, 1975, pp. 149 & 150.

Primary Examiner—James J. Gill
Attorney, Agent, or Firm—Ervin B. Steinberg; Philip J. Feig

[57] ABSTRACT

A method and apparatus for producing on the surface of a workpiece free of contact with a source of energy a pulse shaped ultrasonic shock wave comprise the use of laser means. A plurality of strip-shaped equidistantly spaced surface portions of the workpiece are pulsed with coherent light from the laser means in time delayed sequence. The angle of propagation of the ultrasonic wave is determined by the center-to-center distance between the strip-shaped surface portions illuminated with coherent light, the time delay between the light pulses and the velocity of propagation of the ultrasonic wave in the workpiece.

2 Claims, 5 Drawing Figures

METHOD AND APPARATUS FOR PRODUCING PULSE-SHAPED ACOUSTIC WAVES ON A WORKPIECE SURFACE

SUMMARY OF THE INVENTION

This invention refers to a method and apparatus for producing pulse-shaped plane acoustic waves (shock waves) having a predetermined angle of propagation in a workpiece. More particularly, this invention concerns the production of such waves in light absorbing workpieces which are subjected to nondestructive testing by ultrasonic energy.

When testing workpieces of the type described herein, the ultrasonic shock wave is produced responsive to thermal effects on the surface of the workpiece without physical contact between the source of energy and the workpiece. Moreover, there may exist a considerable distance between the source and the workpiece surface.

The use of laser pulse energy for producing sound waves is known and described, see J. and H. Krautkramer, "Werkstoffprüfung mit Ultraschall" (book), 3rd edition 1975 Springer Verlag, Berlin/Heidelberg, pp. 148 to 150, and U.S. Pat. No. 3,978,713, dated Sept. 7, 1976, issued to C. M. Penney.

When a light absorbing workpiece is illuminated with short light pulses of high intensity, the resulting relatively intense localized heating causes a mechanical stress in the structure of the material, manifesting itself as an elastic wave, i.e. sound wave, which propagates from the illuminated portion of the workpiece surface to the interior of the workpiece. The thickness of the layer which absorbs the light must be thin in relation to the wavelength of the acoustic wave generated. Laser energy sources, providing a beam of coherent light, are preferred means for producing the thermo-acoustic effect. The pulse duration of the laser beam determines the frequency spectrum of the sonic pulse and must be short in relation to the period of the acoustic vibration produced. Utilizing the described generation of a sound wave, i.e. the thermal effect, the direction of propagation of the sound wave is always normal to the surface of the workpiece. Even an arrangement of light rays providing a beam which is incident upon the workpiece surface at an oblique angle causes, due to the large difference between the speed of light and the velocity of sound, an acoustic wave which is propagated along an axis normal to the workpiece surface.

It is possible to impart to the sonic waves a predetermined direction by using a diffraction screen disposed on the workpiece. However, such method then no longer can be considered free of contact. An alternative embodiment comprises projecting upon the workpiece surface by optical means, for instance by a mask disposed in the light path, a pattern of strips. Moreover, it would be possible also to divide the laser beam into two coherent light beam portions which are arranged to produce by interference a striped pattern on the workpiece surface. While these possibilities are known, they have not been used in practice because the direction of propagation of the sound wave is not well-defined but occurs as two symmetrical waves relative to an axis normal to the workpiece surface and, additionally, a non-refracted wave portion (zero diffraction order) still remains.

An object of the present invention is the production of an ultrasonic wave having a predetermined direction of propagation in a workpiece, the generation of the wave being accomplished without physical contact between the source of energy and the workpiece. Such contact-free generation of an ultrasonic wave is particularly necessary when the shape of the workpiece prevents physical contact with the ultrasonic energy source, when the workpiece exhibits a high temperature, or is highly radioactive.

In accordance with the present invention, surface portions of the workpiece are illuminated by means of laser beam energy pulses in a pattern of equidistantly spaced strips to cause the propagation of sound waves. The juxtaposed strips are excited in timed sequence and in a manner that the time delays are chosen for the appropriate phase angles of the individual phase conditions of the acoustic wave. The phase conditions of the wave are a function of the velocity of sound in the workpiece and the predetermined direction of propagation of the wave.

A more detailed explanation of the present invention is provided in the following specification when taken in conjunction with the accompanying drawings.

DETAILED DESCRIPTION OF THE INVENTION

Figure 1:
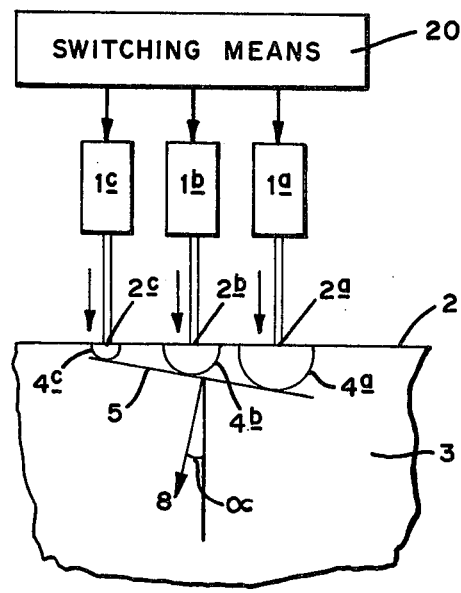
FIG. 1 is a schematic illustration of a preferred embodiment of the invention.

Referring now to the figures and FIG. 1 in particular, a plurality of laser sources $1a$, $1b$, $1c$ are disposed in an array and controlled from a switching means 20 in such a manner that their respective coherent light beams arrive at the surface 2 of a workpiece 3 in predetermined time sequence. The beam from laser source $1a$ produces at the area $2a$, in the configuration of a strip, a sudden heating (heat shock) which in turn causes the propagation of a sound wave $4a$. Somewhat delayed in time the beam from laser source $1b$ provides energy to the area $2b$ and causes also a sound wave $4b$, which is time delayed relative to the acoustic wave $4a$, that is, the sound wave $4a$ already has spread. Once again delayed in time the laser source $1c$ provides energy to the area $2c$ and generates thereat the sound wave $4c$ which is time delayed relative to the preceding waves $4b$ and $4a$. The center of the areas $2a$, $2b$ and $2c$ are equidistantly spaced. By virtue of interference there is generated a wave front 5 having a direction of propagation 8 characterized by angle $\alpha$ relative to an axis normal to the workpiece surface. For the condition of the center-to-center distance d between adjacent laser beams and the velocity of propagation c of the acoustic waves in the workpiece, the time delay t for energizing in sequence the individual laser sources can be determined from the formula:

$$t = (d \times \sin\alpha/c)$$

and using the law of refraction:

$$d \times \sin \alpha = z \times \lambda$$

with only refraction of first order, $z = 1$, being utilized.

Since $\lambda = c \times t$ ($\lambda$ being the wavelength of the acoustic wave) it follows that:

$$d \times \sin \alpha = c \times t$$

$$\text{and } t = (d \times \sin\alpha/c)$$

Thus the time delay between two adjacently disposed laser sources can be calculated from the values of the distance d, the acoustic velocity c and the desired angle of propagation of the ultrasonic wave.

Figure 2:
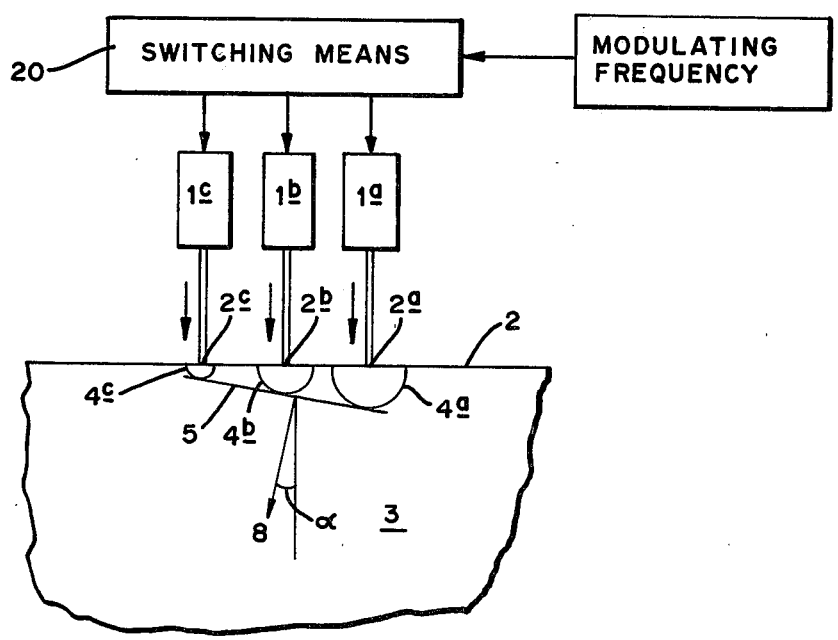
FIG. 2 is a schematic illustration similar to FIG. 1 showing a modification.

A modification, FIG. 2, provides modulating the laser beam during its pulse interval with a signal of suitable frequency. The result is a repetitive propagation of sonic pulses from each individual location while such location is illuminated by the associated laser beam. When the modulation frequency applied to the laser source corresponds to the period of the ultrasonic wave, an acoustic wave train is derived consisting of as many wave trains as pulsations are present in the laser pulse (quasi-harmonic sonic waves). Using the latter arrangement it is possible to produce not only an acoustic shock wave, but also an acoustic wave train limited in time.

Typical Example

Figure 3:
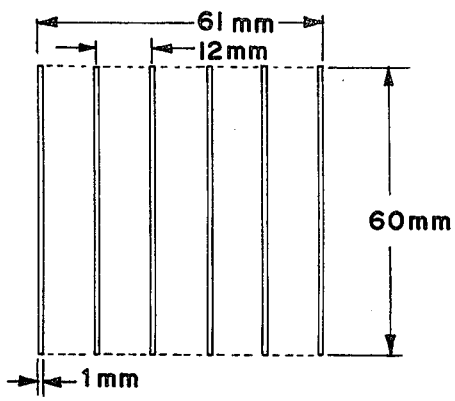
FIG. 3 is an illustration of a typical surface pattern illuminated.

In a typical embodiment of the present invention, six laser sources are used to illuminate six surface strips of a metal workpiece. Each strip is selected to have a dimension of one millimeter width by 60 millimeter length. A beam of this rectangular shape is produced by a pair of crossed cylinder lenses or by one cylinder lens which focusses the beam to one millimeter width and a mask for providing the 60 millimeter gap width. Hence, the area for the acoustic wave generation has a dimension 61 mm by 60 mm, see FIG. 3.

Asumming that $c = 6{,}000$ m/sec (sound velocity) with $\lambda = 6$ mm and $\alpha$ to be 30 degrees: then $d = \lambda /\sin \alpha$ for first order diffraction and $d = 6 \div 0.5 = 12$ mm.

Calculating now the time delay t, $$t = d \times \sin \alpha/c$$

$$t = 12 \text{ mm} \times \sin 30° /6 \times 10^6 \text{mm/sec}$$

$$= 1 \times 10^{-6} \text{ sec} = 1 \ \mu\text{sec}.$$

Figure 4:
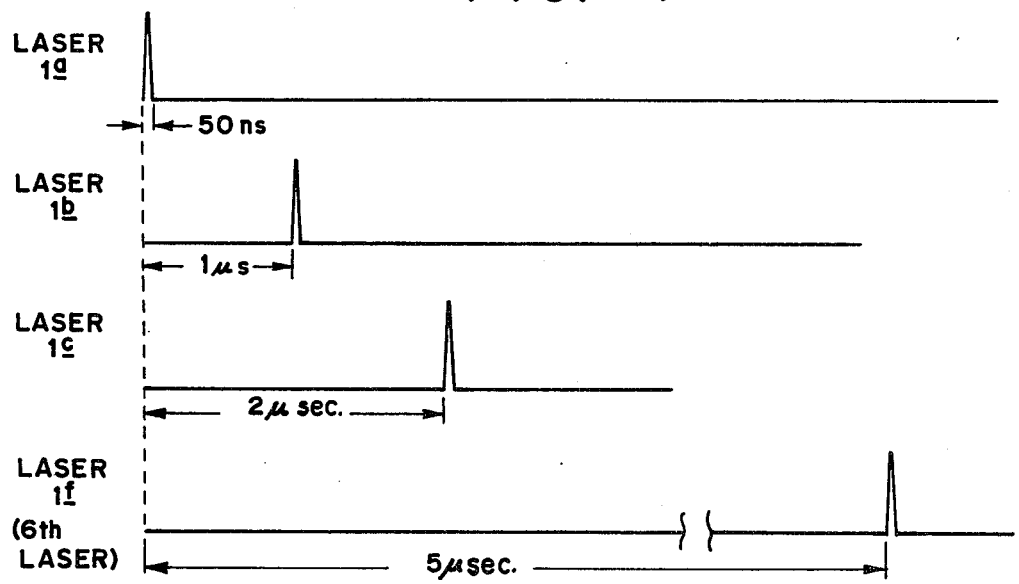
FIG. 4 is a typical timing diagram for the example given.

Hence, the laser sources are triggered at intervals of one microsecond. As it is customary to energize each laser source for at least 50 nanoseconds, a timing sequence as shown in FIG. 4 results, the first laser means 1a being energized every sixth microsecond for 50 nanoseconds.

Figure 5:
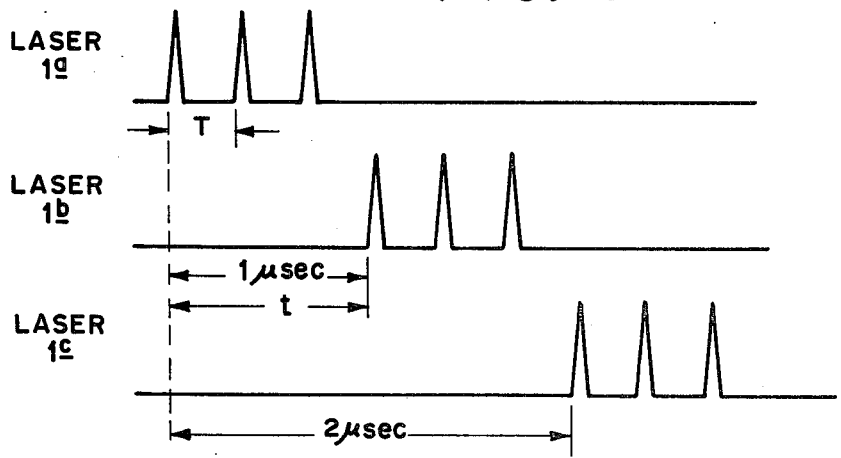
FIG. 5 is a typical timing diagram showing the modulation of the laser source.

FIG. 5 shows the timing diagram when modulation is applied to the laser sources as illustrated in FIG. 2. In this case each laser source is repetitively energized during the time delay interval t to cause the frequency of the acoustic wave f to be equal 1/T wherein T is the period of the laser pulses and therefore of the acoustic wave.

It shall be understood that the above is a typical embodiment of the present invention and that other embodiments may be derived following the above teachings.

What is claimed is:

1. The method of producing free of physical contact on the surface of a light absorbing workpiece an ultrasonic pulse wave having a predetermined angle of propagation relative to an axis normal to the workpiece surface comprising:

illuminating sequentially each of a plurality of equidistantly spaced strip-like portions disposed on the workpiece surface with a respective pulse of coherent radiation;

selecting the time delay between illuminating two adjacent strip-like portions in accordance with the formula:

$$t = d \times \sin\alpha/c$$

wherein:

t is the time delay, d is the center to center distance between two adjacent strip-like portions, $\alpha$ is the angle of propagation of the resulting ultrasonic wave in the workpiece relative to an axis normal to the workpiece surface, and c is the velocity of propagation of the wave in the workpiece, and modulating each pulse of coherent radiation while illuminating a respective strip-like portion, the frequency of said modulating being equal to the period of the ultrasonic wave produced.

2. Apparatus for producing free of physical contact on the surface of a light absorbing workpiece an ultrasonic pulse wave having a predetermined angle of propagation relative to an axis normal to the workpiece surface comprising:

laser means disposed for illuminating with a coherent light beam a plurality of equidistantly spaced strip-like surface portions on the workpiece;

control means coupled to said laser means for causing said laser means to sequentially transmit a pulse of coherent light energy to each of said respective surface portions;

the time delay t between said laser means transmitting a respective pulse to two adjacent surface portions being adjusted for providing the predetermined angle $\alpha$ of propagation of the wave relative to a normal axis intersecting the workpiece surface in accordance with $$\sin \alpha = t \times c/d$$

wherein c is the velocity of propagation of said ultrasonic wave in the workpiece and d is the center-to-center distance between two adjacent strip-like portions, and means coupled to said laser means for modulating each pulse of coherent light with a signal having a frequency equal to the period of the ultrasonic wave.

* * * * *